(12) United States Patent
Peters et al.

(10) Patent No.: US 7,687,523 B2
(45) Date of Patent: Mar. 30, 2010

(54) 3-HETEROARYL-3,9-DIAZABICYCLO[3.3.1]NONANE DERIVATIVES AS NICOTINIC ACETYLCHOLINE RECEPTOR AGONISTS

(75) Inventors: Dan Peters, Malmö (SE); Daniel B. Timmermann, Herlev (DK); Gunnar M. Olsen, Smørum (DK); Elsebet Østergaard Nielsen, København K (DK); Jeppe Kejser Christensen, København N (DK)

(73) Assignee: Neurosearch A/S, Ballerup (DK)

( * ) Notice: Subject to any disclaimer, the term of this patent is extended or adjusted under 35 U.S.C. 154(b) by 0 days.

(21) Appl. No.: 12/087,004

(22) PCT Filed: Feb. 9, 2007

(86) PCT No.: PCT/EP2007/051272
§ 371 (c)(1),
(2), (4) Date: Jun. 24, 2008

(87) PCT Pub. No.: WO2007/090888
PCT Pub. Date: Aug. 16, 2007

(65) Prior Publication Data
US 2009/0005388 A1    Jan. 1, 2009

Related U.S. Application Data

(60) Provisional application No. 60/771,890, filed on Feb. 10, 2006.

(30) Foreign Application Priority Data
Feb. 10, 2006   (DK) ................ 2006 00190

(51) Int. Cl.
*A61K 31/44* (2006.01)
(52) U.S. Cl. ............... 514/338; 544/238; 544/330; 546/268.1
(58) Field of Classification Search ............... 514/338; 544/238, 330; 546/268.1
See application file for complete search history.

(56) References Cited

U.S. PATENT DOCUMENTS

| | | |
|---|---|---|
| 3,196,154 A | 7/1965 | Steck et al. |
| 5,478,939 A | 12/1995 | Trybulski et al. |
| 2003/0225268 A1 | 12/2003 | Bunelle et al. |
| 2005/0101602 A1 | 5/2005 | Basha et al. |

FOREIGN PATENT DOCUMENTS

| | | |
|---|---|---|
| EP | 0 215 650 A2 | 3/1987 |
| EP | 0 952 154 A2 | 10/1999 |
| EP | 1 359 152 A2 | 11/2003 |
| WO | WO-98/54181 A1 | 12/1998 |
| WO | WO-98/54182 A1 | 12/1998 |
| WO | WO-00/34279 A1 | 6/2000 |
| WO | WO-00/44755 A | 8/2000 |
| WO | WO-00/66586 A1 | 11/2000 |
| WO | WO-01/90109 A1 | 11/2001 |
| WO | WO-02/02564 A1 | 1/2002 |
| WO | WO-02/096911 A1 | 12/2002 |
| WO | WO-2005/042501 A1 | 5/2005 |
| WO | WO-2006/045716 A1 | 5/2006 |
| WO | WO-2006/055187 A1 | 5/2006 |
| WO | WO-2006/087306 A2 | 8/2006 |
| WO | WO-2007/065892 A1 | 6/2007 |
| WO | WO-2007/090886 A1 | 8/2007 |
| WO | WO-2007/090887 | 8/2007 |

OTHER PUBLICATIONS

Fales H M et al., J. Am. Chem. Soc. 1954 76(7), pp. 1947-1948.
Edgar A. Steck et al., J. Org. Chem. Sep. 1963 28(9), pp. 2233-2238.
McGuirk P R et al., J. Med. Chem. Feb. 21, 1992 35(4), pp. 611-620.
Barnes R A et al., J. Am. Chem. Soc. Feb. 1953 75, pp. 975-977.
Lucio Toma et al., J. Med. Chem. 2002 45, pp. 4011-4017.

*Primary Examiner*—James O Wilson
*Assistant Examiner*—Douglas M Willis
(74) *Attorney, Agent, or Firm*—Birch, Stewart, Kolasch & Birch, LLP

(57) ABSTRACT

Compounds of the class 3,9-diaza-bicyclo [3.3.1]nonane derivatives. The compounds correspond to structural Formula (I):

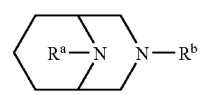

(I)

wherein $R^a$ is hydrogen or optionally substituted alkyl and $R^b$ is a monocyclic heteroaryl group. The compounds are useful in the treatment, prevention, or alleviation of diseases or disorders or conditions that are responsive to modulation of nicotinic acetylcholine receptors, including cognitive disorders, Alzheimer's disease, attention deficit hyperactivity disorder (ADHD), Tourette's syndrome, Bipolar Disorder, obsessive compulsive disorders (OCD), narcolepsy, senile dementia, autism, Parkinson'disease, Amyotrophic Lateral Sclerosis, epilepsy, and diabetic neuropathy.

7 Claims, No Drawings

3-HETEROARYL-3,9-DIAZABICYCLO[3.3.1]NONANE DERIVATIVES AS NICOTINIC ACETYLCHOLINE RECEPTOR AGONISTS

This application is the National Phase of PCT/EP2007/051272 filed on Feb. 9, 2007, which claims priority under 35 U.S.C. 119(e) to U.S. Provisional Application No. 60/771,890 filed on Feb. 10, 2006 and under 35 U.S.C. 119(a) to Patent Application No. PA 2006 00190 filed in Denmark on Feb. 10, 2006. Both of these prior applications are hereby expressly incorporated by reference into the present application.

FIELD OF THE INVENTION

This invention relates to novel 3,9-diazabicyclo[3.3.1]nonane derivatives which are found to be cholinergic ligands at the nicotinic acetylcholine receptors and modulators of the monoamine receptors and transporters. Due to their pharmacological profile the compounds of the invention may be useful for the treatment of diseases or disorders as diverse as those related to the cholinergic system of the central nervous system (CNS), the peripheral nervous system (PNS), diseases or disorders related to smooth muscle contraction, endocrine diseases or disorders, diseases or disorders related to neurodegeneration, diseases or disorders related to inflammation, pain, and withdrawal symptoms caused by the termination of abuse of chemical substances.

BACKGROUND OF THE INVENTION

The endogenous cholinergic neurotransmitter, acetylcholine, exert its biological effect via two types of cholinergic receptors, the muscarinic Acetyl Choline Receptors (mAChR) and the nicotinic Acetyl Choline Receptors (nAChR).

As it is well established that muscarinic acetylcholine receptors dominate quantitatively over nicotinic acetylcholine receptors in the brain area important to memory and cognition, and much research aimed at the development of agents for the treatment of memory related disorders have focused on the synthesis of muscarinic acetylcholine receptor modulators.

Recently, however, an interest in the development of nAChR modulators has emerged. Several diseases are associated with degeneration of the cholinergic system i.e. senile dementia of the Alzheimer type, vascular dementia and cognitive impairment due to the organic brain damage disease related directly to alcoholism. Indeed several CNS disorders can be attributed to a cholinergic deficiency.

U.S. Pat. No. 3,196,154 (Sterling Drug Inc) describes 3-aryl substituted 3,9-methyl-3,9-diazabicyclo[3.3.1]nonanes, and Fales H M & Barnes R A; *J. Am. Chem. Soc.* 1954 76 (7) 1947-1948, describe the synthesis of 9-methyl-3,9-diazatricyclo-[3.3.1.2$^{3,9}$]-undecane. However, the 3,9-diaza-bicyclo[3.3.1]nonane derivatives of the present invention are not suggested.

SUMMARY OF THE INVENTION

In its first aspect, the invention provides 3,9-diaza-bicyclo[3.3.1]nonane derivatives of Formula I:

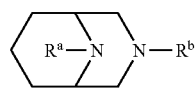

any of its isomers or any mixture of its isomers, or a pharmaceutically acceptable salt thereof; wherein any of its isomers or any mixture of its isomers, or a pharmaceutically acceptable salt thereof; wherein $R^a$ represents hydrogen or alkyl; which alkyl is optionally substituted with one or more substituents independently selected from the group consisting of halo, trifluoromethyl, trifluoromethoxy, cyano, hydroxy, amino, nitro, alkoxy, cycloalkoxy, alkyl, cycloalkyl, cycloalkyl-alkyl, alkenyl and alkynyl; and $R^b$ represents a monocyclic heteroaryl group; which heteroaryl group is optionally substituted with one or more substituents independently selected from the group consisting of halo, trifluoromethyl, trifluoromethoxy, cyano, nitro, hydroxy, alkoxy, cycloalkoxy, alkoxy-alkyl, cycloalkoxy-alkyl, alkenoxy, methylenedioxy, ethylenedioxy, alkyl, cycloalkyl, cycloalkyl-alkyl, alkenyl, alkynyl, alkyl-carbonyl, —NR'R", —(C=O)NR'R" and —NR'(C=O)R"; wherein R' and R" independent of each other are hydrogen or alkyl.

In its second aspect, the invention provides pharmaceutical compositions comprising a therapeutically effective amount of the 3,9-diaza-bicyclo[3.3.1]nonane derivative of the invention, or an isomer or a mixture of its isomers, or a pharmaceutically acceptable salt thereof, or a prodrug thereof, together with at least one pharmaceutically acceptable carrier, excipient or diluent.

In a further aspect, the invention relates to the use of the 3,9-diaza-bicyclo[3.3.1]nonane derivative of the invention, any of its isomers or any mixture of its isomers, or a pharmaceutically acceptable salt thereof, or a prodrug thereof, for the manufacture of a pharmaceutical composition for the treatment, prevention or alleviation of a disease or a disorder or a condition of a mammal, including a human, which disease, disorder or condition is responsive to modulation of the nicotinic acetylcholine receptors.

In a still further aspect, the invention relates to a method for treatment, prevention or alleviation of a disease or a disorder or a condition of a living animal body, including a human, which disorder, disease or condition is responsive to modulation of the nicotinic acetylcholine receptors, which method comprises the step of administering to such a living animal body in need thereof a therapeutically effective amount of the 3,9-diaza-bicyclo[3.3.1]nonane derivative of the invention, any of its isomers or any mixture of its isomers, or a pharmaceutically acceptable salt thereof.

Other objects of the invention will be apparent to the person skilled in the art from the following detailed description and examples.

DETAILED DESCRIPTION OF THE INVENTION

3,9-Diazabicyclo[3.3.1]nonane Derivatives

The present invention is devoted to the provision novel modulators of the nicotinic acetylcholine receptors. In its first aspect, the invention provides 3,9-diaza-bicyclo[3.3.1]nonane derivatives of Formula I:

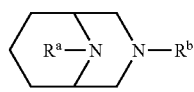
(I)

any of its isomers or any mixture of its isomers, or a pharmaceutically acceptable salt thereof; wherein $R^a$ represents hydrogen or alkyl; which alkyl is optionally substituted with one or more substituents independently selected from the group consisting of halo, trifluoromethyl, trifluoromethoxy, cyano, hydroxy, amino, nitro, alkoxy, cycloalkoxy, alkyl, cycloalkyl, cycloalkyl-alkyl, alkenyl and alkynyl; and $R^b$ represents a monocyclic heteroaryl group; which heteroaryl group is optionally substituted with one or more substituents independently selected from the group consisting of halo, trifluoromethyl, trifluoromethoxy, cyano, nitro, hydroxy, alkoxy, cycloalkoxy, alkoxy-alkyl, cycloalkoxy-alkyl, alkenoxy, methylenedioxy, ethylenedioxy, alkyl, cycloalkyl, cycloalkyl-alkyl, alkenyl, alkynyl, alkyl-carbonyl, —NR'R", —(C=O)NR'R" and —NR'(C=O)R"; wherein R' and R" independent of each other are hydrogen or alkyl.

In a preferred embodiment the 3,9-diaza-bicyclo[3.3.1]nonane derivative of the invention is a compound of Formula I, wherein $R^a$ represents hydrogen or alkyl; which alkyl is optionally substituted with one or more substituents independently selected from the group consisting of halo, trifluoromethyl, trifluoromethoxy, cyano, hydroxy, amino, nitro, alkoxy, cycloalkoxy, alkyl, cycloalkyl, cycloalkyl-alkyl, alkenyl and alkynyl; and $R^b$ represents a monocyclic heteroaryl group; which heteroaryl group is optionally substituted with one or more substituents independently selected from the group consisting of halo, trifluoromethyl, trifluoromethoxy, cyano, nitro, hydroxy, alkoxy, cycloalkoxy, alkoxy-alkyl, cycloalkoxy-alkyl, methylenedioxy, ethylenedioxy, alkyl, cycloalkyl, cycloalkyl-alkyl, alkenyl, alkynyl, —NR'R", —(C=O)NR'R" and —NR'(C=O)R"; wherein R' and R" independent of each other are hydrogen or alkyl.

In another preferred embodiment the 3,9-diaza-bicyclo[3.3.1]nonane derivative of the invention is a compound of Formula I, wherein $R^a$ represents hydrogen or alkyl.

In a more preferred embodiment $R^a$ represents hydrogen or methyl.

In a still more preferred embodiment $R^a$ represents hydrogen.

In another more preferred embodiment $R^a$ represents alkyl, in particular methyl, ethyl, propyl or isopropyl.

In an even more preferred embodiment $R^a$ represents methyl.

In a third preferred embodiment the 3,9-diaza-bicyclo[3.3.1]nonane derivative of the invention is a compound of Formula I, wherein $R^b$ represents a 5-membered monocyclic heteroaryl group of Formula Ia, Ib or Ic:

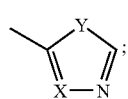
(Ia)

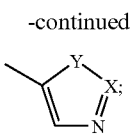
(Ib)

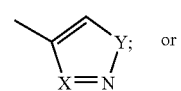
(Ic)

a 6-membered monocyclic heteroaryl group of Formula Id or Ie:

(Id)

(Ie)

wherein X and Z, independently of each other, represent CH or N; and Y represents O, S, Se or NH; and which heteroaryl group is optionally substituted with one or more substituents independently selected from the group consisting of halo, trifluoromethyl, trifluoromethoxy, cyano, nitro, hydroxy, alkoxy, cycloalkoxy, alkoxy-alkyl, cycloalkoxy-alkyl, alkenoxy, methylenedioxy, ethylenedioxy, alkyl, cycloalkyl, cycloalkyl-alkyl, alkenyl, alkynyl, alkyl-carbonyl, —NR'R", —(C=O)NR'R" and —NR'(C=O)R"; wherein R' and R" independent of each other are hydrogen or alkyl.

In a more preferred embodiment $R^b$ represents a 5-membered monocyclic heteroaryl group of Formula Ia, Ib or Ic:

(Ia)

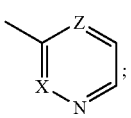
(Ib)

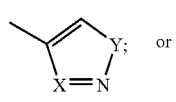
(Ic)

a 6-membered monocyclic heteroaryl group of Formula Id:

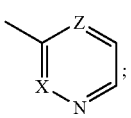
(Id)

wherein X and Z, independently of each other, represent CH or N; and Y represents O, S, Se or NH; and which heteroaryl group is optionally substituted once or twice with substituents selected from the group consisting of halo, trifluoromethyl, trifluoromethoxy, cyano, nitro, hydroxy, alkoxy, cycloalkoxy, alkoxy-alkyl, cycloalkoxy-alkyl, methylenedioxy, ethylenedioxy, alkyl, cycloalkyl, cycloalkyl-alkyl, alkenyl, alkynyl, —NR'R", —(C=O)NR'R" and —NR'(C=O)R"; wherein R' and R" independent of each other are hydrogen or alkyl.

In an even more preferred embodiment $R^b$ represents a 5-membered monocyclic heteroaryl group selected from oxazolyl, thiazolyl, imidazolyl, pyrazolyl, isoxazolyl, isothiazolyl, 1,2,3-oxadiazolyl, 1,2,3-triazolyl, or 1,3,4-thiadiazolyl; or a 6-membered monocyclic heteroaryl group selected from pyridinyl, pyridazinyl, pyrimidinyl or pyrazinyl; and which heteroaryl group is optionally substituted once or twice with substituents independently selected from the group consisting of halo, trifluoromethyl, trifluoromethoxy, cyano, nitro, hydroxy, alkoxy, cycloalkoxy, alkoxy-alkyl, cycloalkoxy-alkyl, alkenoxy, methylenedioxy, ethylenedioxy, alkyl, cycloalkyl, cycloalkyl-alkyl, alkenyl, alkynyl, alkyl-carbonyl, —NR'R", —(C=O)NR'R" and —NR'(C=O)R"; wherein R' and R" independent of each other are hydrogen or alkyl.

In a still more preferred embodiment $R^b$ represents a 5-membered monocyclic heteroaryl group selected from oxazolyl, thiazolyl, imidazolyl, pyrazolyl, isoxazolyl, isothiazolyl, 1,2,3-oxadiazolyl, 1,2,3-triazolyl, or 1,3,4-thiadiazolyl; or a 6-membered monocyclic heteroaryl group selected from pyridinyl, pyridazinyl, pyrimidinyl or pyrazinyl; and which heteroaryl groups are optionally substituted once or twice with substituents selected from the group consisting of halo, trifluoromethyl, trifluoromethoxy, cyano, nitro, hydroxy, alkoxy, cycloalkoxy, alkoxy-alkyl, cycloalkoxy-alkyl, methylenedioxy, ethylenedioxy, alkyl, cycloalkyl, cycloalkyl-alkyl, alkenyl, alkynyl, —NR'R", —(C=O)NR'R" and —NR'(C=O)R"; wherein R' and R" independent of each other are hydrogen or alkyl.

In a yet more preferred embodiment $R^b$ represents an optionally substituted 5-membered monocyclic heteroaryl group selected from oxazolyl, thiazolyl, imidazolyl, pyrazolyl, isoxazolyl, isothiazolyl, 1,2,3-oxadiazolyl, 1,2,3-triazolyl and 1,3,4-thiadiazolyl.

In a further more preferred embodiment $R^b$ represents an optionally substituted 5-membered monocyclic heteroaryl group selected from oxazolyl, thiazolyl, isoxazolyl, isothiazolyl, 1,2,3-oxadiazolyl and 1,3,4-thiadiazolyl.

In a yet further more preferred embodiment $R^b$ represents an optionally substituted 6-membered monocyclic heteroaryl group selected from pyridinyl, pyridazinyl, pyrimidinyl and pyrazinyl.

In a yet further more preferred embodiment $R^b$ represents pyridinyl, pyridazinyl or pyrimidinyl.

In a yet further more preferred embodiment $R^b$ represents pyridinyl, in particular pyridine-2-yl or pyridine-3-yl.

In a yet further more preferred embodiment $R^b$ represents pyridazinyl, in particular pyridazin-3-yl.

In a yet further more preferred embodiment $R^b$ represents pyrimidinyl, in particular pyrimidin-2-yl.

In a yet further more preferred embodiment the 3,9-diaza-bicyclo[3.3.1]nonane derivative of the invention is a compound as described above, wherein the monocyclic heteroaryl group is optionally substituted once or twice with substituents selected from halo, trifluoromethyl, trifluoromethoxy, cyano, nitro, hydroxy, alkoxy, alkenoxy, alkyl, cycloalkyl and alkyl-carbonyl.

In a more preferred embodiment the monocyclic heteroaryl group is optionally substituted once or twice with substituents selected from halo, trifluoromethyl, trifluoromethoxy, cyano, nitro, hydroxy, alkoxy, alkyl and cycloalkyl.

In an even more preferred embodiment the monocyclic heteroaryl group is optionally substituted with halo, trifluoromethyl, alkoxy, alkenoxy and alkyl-carbonyl.

In a still more preferred embodiment the monocyclic heteroaryl group is optionally substituted with halo or trifluoromethyl.

In a further more preferred embodiment the 3,9-diaza-bicyclo[3.3.1]nonane derivative of the invention is a compound as described above, wherein $R^b$ represents pyridinyl, pyridazinyl or pyrimidinyl, optionally substituted once or twice with halo, trifluoromethyl, alkoxy, alkenoxy and/or alkyl-carbonyl.

In a more preferred embodiment $R^b$ represents pyridinyl, in particular pyridin2-yl or pyridine-3-yl, optionally substituted once or twice with halo, in particular fluoro, chloro, bromo or iodo, trifluoromethyl, alkoxy, in particular methoxy or ethoxy, alkenoxy, in particular vinyloxy or propenyloxy, and alkyl-carbonyl, in particular methyl-carbonyl.

In another more preferred embodiment $R^b$ represents pyridazinyl, in particular pyridazin-3-yl, optionally substituted with halo, in particular fluoro, chloro, bromo or iodo, trifluoromethyl, alkoxy, in particular methoxy or ethoxy, alkenoxy, in particular vinyloxy or propenyloxy, and alkyl-carbonyl, in particular methyl-carbonyl.

In a third more preferred embodiment $R^b$ represents pyrimidinyl, in particular pyrimidin-2-yl, optionally substituted with halo, in particular fluoro, chloro, bromo or iodo, trifluoromethyl, alkoxy, in particular methoxy or ethoxy, alkenoxy, in particular vinyloxy or propenyloxy, and alkyl-carbonyl, in particular methyl-carbonyl.

In a fourth more preferred embodiment $R^b$ represents pyridinyl, optionally substituted with halo, in particular fluoro, chloro, bromo or iodo, or with trifluoromethyl.

In a most preferred embodiment the 3,9-diaza-bicyclo[3.3.1]nonane derivative of the invention is 3-(5-Chloro-pyridin-3-yl)-9-methyl-3,9-diaza-bicyclo[3.3.1]nonane;

9-Methyl-3-pyridin-3-yl-3,9-diaza-bicyclo[3.3.1]nonane;

3-Pyridin-3-yl-3,9-diaza-bicyclo[3.3.1]nonane;

3-(5-Chloro-pyridin-2-yl)-9-methyl-3,9-diaza-bicyclo[3.3.1]nonane;

3-(6-Chloro-pyridin-2-yl)-9-methyl-3,9-diaza-bicyclo[3.3.1]nonane;

3-(6-Bromo-pyridin-2-yl)-9-methyl-3,9-diaza-bicyclo[3.3.1]nonane;

3-(5-Bromo-pyridin-2-yl)-9-methyl-3,9-diaza-bicyclo[3.3.1]nonane;

3-(6-Chloro-pyridazin-3-yl)-9-methyl-3,9-diaza-bicyclo[3.3.1]nonane;

3-(6-Bromo-pyridazin-3-yl)-9-methyl-3,9-diaza-bicyclo[3.3.1]nonane;

3-(5-Ethoxy-pyridin-3-yl)-9-methyl-3,9-diaza-bicyclo[3.3.1]nonane;

3-(5-Methoxy-pyridin-3-yl)-9-methyl-3,9-diaza-bicyclo[3.3.1]nonane;

9-Methyl-3-(5-vinyloxy-pyridin-3-yl)-3,9-diaza-bicyclo[3.3.1]nonane;

9-Methyl-3-{5-[((Z)-propenyl)oxy]-pyridin-3-yl}-3,9-diaza-bicyclo[3.3.1]nonane;

3-(5-Iodo-pyridin-2-yl)-9-methyl-3,9-diaza-bicyclo[3.3.1]nonane;

3-(3,5-Dichloro-pyridin-2-yl)-9-methyl-3,9-diaza-bicyclo[3.3.1]nonane;

1-[6-(9-Methyl-3,9-diaza-bicyclo[3.3.1]non-3-yl)-pyridin-2-yl]-ethanone;

1-[6-(9-Methyl-3,9-diaza-bicyclo[3.3.1]non-3-yl)-pyridin-2-yl]-ethanone;

3-(5-Bromo-pyrimidin-2-yl)-9-methyl-3,9-diaza-bicyclo[3.3.1]nonane;

3-(6-Chloro-pyridin-3-yl)-9-methyl-3,9-diaza-bicyclo[3.3.1]nonane;

3-(5-Chloro-pyridin-2-yl)-3,9-diaza-bicyclo[3.3.1]nonane;

3-Pyridin-2-yl-3,9-diaza-bicyclo[3.3.1]nonane;

3-(3,5-Dichloro-pyridin-2-yl)-3,9-diaza-bicyclo[3.3.1]nonane;

9-Methyl-3-pyridazin-3-yl-3,9-diaza-bicyclo[3.3.1]nonane;

3-(6-Bromo-pyridin-3-yl)-9-methyl-3,9-diaza-bicyclo[3.3.1]nonane; or 9,9-Dimethyl-3-(6-bromo-pyridin-3-yl)-3,9-diaza-bicyclo[3.3.1]nonane;

or a pharmaceutically acceptable salt thereof.

Any combination of two or more of the embodiments as described above is considered within the scope of the present invention.

Definition of Substituents

In the context of this invention halo represents fluoro, chloro, bromo or iodo.

In the context of this invention an alkyl group designates a univalent saturated, straight or branched hydrocarbon chain. The hydrocarbon chain preferably contains of from one to six carbon atoms ($C_{1-6}$-alkyl), including pentyl, isopentyl, neopentyl, tertiary pentyl, hexyl and isohexyl. In a preferred embodiment alkyl represents a $C_{1-4}$-alkyl group, including butyl, isobutyl, secondary butyl, and tertiary butyl. In another preferred embodiment of this invention alkyl represents a $C_{1-3}$-alkyl group, which may in particular be methyl, ethyl, propyl or isopropyl.

In the context of this invention an alkenyl group designates a carbon chain containing one or more double bonds, including di-enes, tri-enes and poly-enes. In a preferred embodiment the alkenyl group of the invention comprises of from two to six carbon atoms ($C_{2-6}$-alkenyl), including at least one double bond. In a most preferred embodiment the alkenyl group of the invention is ethenyl; 1- or 2-propenyl; 1-, 2- or 3-butenyl, or 1,3-butadienyl; 1-, 2-, 3-, 4- or 5-hexenyl, or 1,3-hexadienyl, or 1,3,5-hexatrienyl.

In the context of this invention an alkynyl group designates a carbon chain containing one or more triple bonds, including di-ynes, tri-ynes and poly-ynes. In a preferred embodiment the alkynyl group of the invention comprises of from two to six carbon atoms ($C_{2-6}$-alkynyl), including at least one triple bond. In its most preferred embodiment the alkynyl group of the invention is ethynyl; 1-, or 2-propynyl; 1-, 2-, or 3-butynyl, or 1,3-butadiynyl; 1-, 2-, 3-, 4-pentynyl, or 1,3-pentadiynyl; 1-, 2-, 3-, 4-, or 5-hexynyl, or 1,3-hexadiynyl or 1,3,5-hexatriynyl.

In the context of this invention a cycloalkyl group designates a cyclic alkyl group, preferably containing of from three to seven carbon atoms ($C_{3-7}$-cycloalkyl), including cyclopropyl, cyclobutyl, cyclopentyl, cyclohexyl and cycloheptyl.

In the context of this invention an alkoxy group designates an "alkyl-O—" group, wherein alkyl is as defined above. Examples of preferred alkoxy groups of the invention include methoxy and ethoxy.

In the context of this invention an alkenoxy group designates an "alkenyl-O—" group, wherein alkenyl is as defined above. Examples of preferred alkenoxy groups of the invention include vinyloxy and propenyloxy.

In the context of this invention a cycloalkoxy group designates a "cycloalkyl-O—" group, wherein cycloalkyl is as defined above. A preferred alkoxy group of the invention is cyclopropoxy.

In the context of this invention a cycloalkyl-alkyl group designates a cycloalkyl group as defined above, which cycloalkyl group is substituted on an alkyl group as also defined above. Examples of preferred cycloalkyl-alkyl groups of the invention include cyclopropylmethyl and cyclopropylethyl.

In the context of this invention an alkyl-carbonyl group designates an "alkyl-(CO)—" group, wherein alkyl is as defined above. Examples of preferred alkyl-carbonyl groups of the invention include methyl-carbonyl (acetyl) and ethyl-carbonyl.

In the context of this invention a monocyclic heteroaryl designates an aromatic heterocyclic group, which holds one or more heteroatoms in its ring structure. Preferred heteroatoms include nitrogen (N), oxygen (O), and sulphur (S), and preferred monocyclic heteroaryl groups of the invention are 5-6 membered heteroaryl groups.

Preferred 5-membered heteroaryl groups of the invention include oxazolyl, thiazolyl, imidazolyl, pyrazolyl, isoxazolyl, isothiazolyl, 1,2,3-oxadiazolyl, 1,2,3-triazolyl, and 1,3,4-thiadiazolyl, and preferred 6-membered monocyclic heteroaryl groups of the invention include pyridinyl (in particular pyridin2-yl or pyridine-3-yl), pyridazinyl (in particular pyridazin-3-yl), pyrimidinyl (in particular pyrimidin-2-yl) and pyrazinyl (in particular pyrazin-3-yl).

Pharmaceutically Acceptable Salts

The 3,9-diazabicyclo[3.3.1]nonane derivatives of the invention may be provided in any form suitable for the intended administration. Suitable forms include pharmaceutically (i.e. physiologically) acceptable salts, and pre- or pro-drug forms of the 3,9-diazabicyclo[3.3.1]nonane derivative of the invention.

Examples of pharmaceutically acceptable addition salts include, without limitation, the non-toxic inorganic and organic acid addition salts such as the hydrochloride derived from hydrochloric acid, the hydrobromide derived from hydrobromic acid, the nitrate derived from nitric acid, the perchlorate derived from perchloric acid, the phosphate derived from phosphoric acid, the sulphate derived from sulphuric acid, the formate derived from formic acid, the acetate derived from acetic acid, the aconate derived from aconitic acid, the ascorbate derived from ascorbic acid, the benzenesulphonate derived from benzensulphonic acid, the benzoate derived from benzoic acid, the cinnamate derived from cinnamic acid, the citrate derived from citric acid, the embonate derived from embonic acid, the enantate derived from enanthic acid, the fumarate derived from fumaric acid, the glutamate derived from glutamic acid, the glycolate derived from glycolic acid, the lactate derived from lactic acid, the maleate derived from maleic acid, the malonate derived from malonic acid, the mandelate derived from mandelic acid, the methanesulphonate derived from methane sulphonic acid, the naphthalene-2-sulphonate derived from naphtalene-2-sulphonic acid, the phthalate derived from phthalic acid, the salicylate derived from salicylic acid, the sorbate derived from sorbic acid, the stearate derived from stearic acid, the succinate derived from succinic acid, the tartrate derived from tartaric acid, the toluene-p-sulphonate derived from p-toluene sulphonic acid, and the like. Such salts may be formed by procedures well known and described in the art.

Other acids such as oxalic acid, which may not be considered pharmaceutically acceptable, may be useful in the preparation of salts useful as intermediates in obtaining a chemical compound of the invention and its pharmaceutically acceptable acid addition salt.

Additional examples of pharmaceutically acceptable addition salts include, without limitation, the non-toxic inorganic and organic acid addition salts such as the hydrochloride, the hydrobromide, the nitrate, the perchlorate, the phosphate, the sulphate, the formate, the acetate, the aconate, the ascorbate, the benzene-sulphonate, the benzoate, the cinnamate, the citrate, the embonate, the enantate, the fumarate, the glutamate, the glycolate, the lactate, the maleate, the malonate, the mandelate, the methanesulphonate, the naphthalene-2-sulphonate, the phthalate, the salicylate, the sorbate, the stearate, the succinate, the tartrate, the toluene-p-sulphonate, and the like. Such salts may be formed by procedures well known and described in the art.

Examples of pharmaceutically acceptable cationic salts of a 3,9-diazabicyclo[3.3.1]nonane derivative of the invention include, without limitation, the sodium, the potassium, the calcium, the magnesium, the zinc, the aluminium, the lithium, the choline, the lysinium, and the ammonium salt, and the like, of a chemical compound of the invention containing an anionic group. Such cationic salts may be formed by procedures well known and described in the art.

In the context of this invention the "onium salts" of N-containing compounds are also contemplated as pharmaceutically acceptable salts. Preferred "onium salts" include the alkyl-onium salts, the cycloalkyl-onium salts, and the cycloalkylalkyl-onium salts.

Examples of pre- or prodrug forms of the 3,9-diazabicyclo[3.3.1]nonane derivative of the invention include examples of suitable prodrugs of the substances according to the invention include compounds modified at one or more reactive or derivatizable groups of the parent compound. Of particular interest are compounds modified at a carboxyl group, a hydroxyl group, or an amino group. Examples of suitable derivatives are esters or amides.

The 3,9-diazabicyclo[3.3.1]nonane derivative of the invention may be provided in dissoluble or indissoluble forms together with a pharmaceutically acceptable solvent such as water, ethanol, and the like. Dissoluble forms may also include hydrated forms such as the monohydrate, the dihydrate, the hemihydrate, the trihydrate, the tetrahydrate, and the like. In general, the dissoluble forms are considered equivalent to indissoluble forms for the purposes of this invention.

Isomers

It will be appreciated by those skilled in the art that the 3,9-diazabicyclo[3.3.1]nonane derivatives of the present invention may exist in different stereoisomeric forms, including enantiomers, diastereomers, as well as geometric isomers (cis-trans isomers). The invention includes all such isomers and any mixtures thereof including racemic mixtures.

Racemic forms can be resolved into the optical antipodes by known methods and techniques. One way of separating the isomeric salts is by use of an optically active acid, and liberating the optically active amine compound by treatment with a base. Another method for resolving racemates into the optical antipodes is based upon chromatography on an optical active matrix. Racemic compounds of the present invention can thus be resolved into their optical antipodes, e.g., by fractional crystallisation of d- or l- (tartrates, mandelates, or camphorsulphonate) salts for example.

The chemical compounds of the present invention may also be resolved by the formation of diastereomeric amides by reaction of the chemical compounds of the present invention with an optically active activated carboxylic acid such as that derived from (+) or (−) phenylalanine, (+) or (−) phenylglycine, (+) or (−) camphanic acid or by the formation of diastereomeric carbamates by reaction of the chemical compound of the present invention with an optically active chloroformate or the like.

Additional methods for the resolving the optical isomers are known in the art. Such methods include those described by Jaques J, Collet A, & Wilen S in "*Enantiomers, Racemates, and Resolutions*", John Wiley and Sons, New York (1981).

Optical active compounds can also be prepared from optical active starting materials.

Labelled Compounds

The 3,9-diazabicyclo[3.3.1]nonane derivatives of the invention may be used in their labelled or unlabelled form. In the context of this invention the labelled compound has one or more atoms replaced by an atom having an atomic mass or mass number different from the atomic mass or mass number usually found in nature. The labelling will allow easy quantitative detection of said compound.

The labelled compounds of the invention may be useful as diagnostic tools, radio tracers, or monitoring agents in various diagnostic methods, and for in vivo receptor imaging.

The labelled isomer of the invention preferably contains at least one radio-nuclide as a label. Positron emitting radionuclides are all candidates for usage. In the context of this invention the radionuclide is preferably selected from $^2$H (deuterium), $^3$H (tritium), $^{13}$C, $^{14}$C, $^{131}$I, $^{125}$I, $^{123}$I, and $^{18}$F.

The physical method for detecting the labelled isomer of the present invention may be selected from Position Emission Tomography (PET), Single Photon Imaging Computed Tomography (SPECT), Magnetic Resonance Spectroscopy (MRS), Magnetic Resonance Imaging (MRI), and Computed Axial X-ray Tomography (CAT), or combinations thereof.

Preferred labelled 3,9-diazabicyclo[3.3.1]nonane derivatives of the invention include 3-(6-Fluoro-pyridin-3-yl)-9-methyl-3,9-diaza-bicyclo[3.3.1]nonane and 3-(6-Iodo-pyridin-3-yl)-9-methyl-3,9-diaza-bicyclo[3.3.1]nonane.

Methods of Preparation

The 3,9-diazabicyclo[3.3.1]nonane derivatives of the invention may be prepared by conventional methods for chemical synthesis, e.g. those described in the working examples. The starting materials for the processes described in the present application are known or may readily be prepared by conventional methods from commercially available chemicals.

Also one compound of the invention can be converted to another compound of the invention using conventional methods.

The end products of the reactions described herein may be isolated by conventional techniques, e.g. by extraction, crystallisation, distillation, chromatography, etc.

Biological Activity

The present invention is devoted to the provision novel ligands and modulators of the nicotinic receptors, and modulators of the monoamine receptors, in particular the biogenic amine transporters such as the serotonin receptor (5-HTR), the dopamine receptor (DAR) and the norepinephrine receptor (NER), and of the biogenic amine transporters for serotonin (5-HT), dopamine (DA) and norepinephrine (NE).

The 3,9-diazabicyclo[3.3.1]nonane derivatives of the invention therefore are considered useful for the treatment of diseases or disorders as diverse as those related to the cholinergic system of the central nervous system (CNS), the peripheral nervous system (PNS), diseases or disorders related to smooth muscle contraction, endocrine diseases or disorders, diseases or disorders related to neuro-degeneration, diseases or disorders related to inflammation, pain, and withdrawal symptoms caused by the termination of abuse of chemical substances.

In a preferred embodiment the compounds of the present invention may be useful for the treatment, prevention or alleviation of a cognitive disorder, learning deficit, memory deficits and dysfunction, Alzheimer's disease, attention deficit, attention deficit hyperactivity disorder (ADHD), Tourette's syndrome, psychosis, depression, bipolar disorder, mania, manic depression, schizophrenia, cognitive or attention deficits related to schizophrenia, obsessive compulsive disorders (OCD), panic disorders, eating disorders such as anorexia nervosa, bulimia and obesity, narcolepsy, nociception, AIDS-dementia, senile dementia, autism, Parkinson's disease, Huntington's disease, Amyotrophic Lateral Sclerosis, anxiety, non-OCD anxiety disorders, convulsive disorders, epilepsy, neurodegenerative disorders, transient anoxia, induced neuro-degeneration, neuropathy, diabetic neuropathy, periferic dyslexia, tardive dyskinesia, hyperkinesia, mild, pain, moderate or severe pain, pain of acute, chronic or recurrent character, pain caused by migraine, postoperative pain, phantom limb pain, inflammatory pain, neuropathic pain, chronic headache, central pain, pain related to diabetic neuropathy, to post therapeutic neuralgia, or to peripheral nerve injury, bulimia, post-traumatic syndrome, social phobia, sleeping disorders, pseudodementia, Ganser's syndrome, pre-menstrual syndrome, late luteal phase syndrome, chronic fatigue syndrome, mutism, trichotillomania, jet-lag, arrhythmias, smooth muscle contractions, angina pectoris, premature labour, diarrhoea, asthma, tardive dyskinesia, hyperkinesia, premature ejaculation, erectile difficulty, hypertension, inflammatory disorders, inflammatory skin disorders, acne, rosacea, Chron's disease, inflammatory bowel disease, ulcerative colitis, diarrhoea, or withdrawal symptoms caused by termination of use of addictive substances, including nicotine containing products such as tobacco, opioids such as heroin, cocaine and morphine, benzodiazepines and benzodiazepine-like drugs, and alcohol.

In a more preferred embodiment the 3,9-diazabicyclo[3.3.1]nonane derivatives of the invention may be useful for the treatment, prevention or alleviation of pain, mild or moderate or even severe pain, pain of acute, chronic or recurrent character, pain caused by migraine, postoperative pain, phantom limb pain, inflammatory pain, neuropathic pain, chronic headache, central pain, pain related to diabetic neuropathy, to post therapeutic neuralgia, or to peripheral nerve injury.

In an even more preferred embodiment the 3,9-diazabicyclo[3.3.1]nonane derivatives of the invention may be useful for the treatment, prevention or alleviation of diseases, disorders or conditions associated with smooth muscle contractions, convulsive disorders, angina pectoris, premature labour, convulsions, diarrhoea, asthma, epilepsy, tardive dyskinesia, hyperkinesia, premature ejaculation, or erectile difficulty.

In a still more preferred embodiment the 3,9-diazabicyclo[3.3.1]nonane derivatives of the invention may be useful for the treatment, prevention or alleviation of a neurodegenerative disorder, transient anoxia, or induced neuro-degeneration.

In a yet more preferred embodiment the 3,9-diazabicyclo[3.3.1]nonane derivatives of the invention may be useful for the treatment, prevention or alleviation of an inflammatory disorder, inflammatory skin disorder, acne, rosacea, Chron's disease, inflammatory bowel disease, ulcerative colitis, or diarrhoea.

In a further preferred embodiment the 3,9-diazabicyclo[3.3.1]nonane derivatives of the invention may be useful for the treatment, prevention or alleviation of diabetic neuropathy, schizophrenia, cognitive or attentional deficits related to schizophrenia, or depression.

In a still further preferred embodiment the 3,9-diazabicyclo[3.3.1]nonane derivatives of the invention may be useful for the treatment, prevention or alleviation of pain, in particular neuropathic pain, diabetic neuropathy, schizophrenia and cognitive or attentional deficits related to schizophrenia, depression, and for assisting in obtaining smoking cessation.

Finally the 3,9-diazabicyclo[3.3.1]nonane derivatives of the invention may be useful for the treatment of withdrawal symptoms caused by termination of use of addictive substances. Such addictive substances include nicotine containing products such as tobacco, opioids such as heroin, cocaine and morphine, benzodiazepines, benzodiazepine-like drugs, and alcohol. Withdrawal from addictive substances is in general a traumatic experience characterised by anxiety and frustration, anger, anxiety, difficulties in concentrating, restlessness, decreased heart rate and increased appetite and weight gain.

In this context "treatment" covers treatment, prevention, prophylactics and alleviation of withdrawal symptoms and abstinence as well as treatment resulting in a voluntary diminished intake of the addictive substance.

The 3,9-diazabicyclo[3.3.1]nonane derivatives of the invention may also be useful as diagnostic tools or monitoring agents in various diagnostic methods, and in particular for in vivo receptor imaging (neuroimaging), and they may be used in labelled or unlabelled form.

It is at present contemplated that a suitable dosage of the active pharmaceutical ingredient (API) is within the range of from about 0.1 to about 1000 mg API per day, more preferred of from about 10 to about 500 mg API per day, most preferred of from about 30 to about 100 mg API per day, dependent, however, upon the exact mode of administration, the form in which it is administered, the indication considered, the subject and in particular the body weight of the subject involved, and further the preference and experience of the physician or veterinarian in charge.

Preferred compounds of the invention show a biological activity in the sub-micromolar and micromolar range, i.e. of from below 1 to about 100 µM.

Pharmaceutical Compositions

In another aspect the invention provides novel pharmaceutical compositions comprising a therapeutically effective amount of a 3,9-diazabicyclo[3.3.1]nonane derivative of the invention.

While a 3,9-diazabicyclo[3.3.1]nonane derivative of the invention for use in therapy may be administered in the form of the raw chemical compound, it is preferred to introduce the active ingredient, optionally in the form of a physiologically acceptable salt, in a pharmaceutical composition together with one or more adjuvants, excipients, carriers, buffers, diluents, and/or other customary pharmaceutical auxiliaries.

In a preferred embodiment, the invention provides pharmaceutical compositions comprising the 3,9-diazabicyclo[3.3.1]nonane derivative of the invention, or a pharmaceutically acceptable salt or derivative thereof, together with one or more pharmaceutically acceptable carriers, and, optionally, other therapeutic and/or prophylactic ingredients, known and used in the art. The carrier(s) must be "acceptable" in the sense of being compatible with the other ingredients of the formulation and not harmful to the recipient thereof.

Pharmaceutical compositions of the invention may be those suitable for oral, rectal, bronchial, nasal, pulmonal, topical (including buccal and sub-lingual), transdermal, vaginal or parenteral (including cutaneous, subcutaneous, intramuscular, intraperitoneal, intravenous, intraarterial, intracerebral, intraocular injection or infusion) administration, or those in a form suitable for administration by inhalation or insufflation, including powders and liquid aerosol administration, or by sustained release systems. Suitable examples of sustained release systems include semipermeable matrices of solid hydrophobic polymers containing the compound of the invention, which matrices may be in form of shaped articles, e.g. films or microcapsules.

The chemical compound of the invention, together with a conventional adjuvant, carrier, or diluent, may thus be placed into the form of pharmaceutical compositions and unit dosages thereof. Such forms include solids, and in particular tablets, filled capsules, powder and pellet forms, and liquids, in particular aqueous or non-aqueous solutions, suspensions, emulsions, elixirs, and capsules filled with the same, all for oral use, suppositories for rectal administration, and sterile injectable solutions for parenteral use. Such pharmaceutical compositions and unit dosage forms thereof may comprise conventional ingredients in conventional proportions, with or without additional active compounds or principles, and such unit dosage forms may contain any suitable effective amount of the active ingredient commensurate with the intended daily dosage range to be employed.

The chemical compound of the present invention can be administered in a wide variety of oral and parenteral dosage forms. It will be obvious to those skilled in the art that the following dosage forms may comprise, as the active component, either a chemical compound of the invention or a pharmaceutically acceptable salt of a chemical compound of the invention.

For preparing pharmaceutical compositions from a chemical compound of the present invention, pharmaceutically acceptable carriers can be either solid or liquid. Solid form preparations include powders, tablets, pills, capsules, cachets, suppositories, and dispersible granules. A solid carrier can be one or more substances which may also act as diluents, flavouring agents, solubilizers, lubricants, suspending agents, binders, preservatives, tablet disintegrating agents, or an encapsulating material.

In powders, the carrier is a finely divided solid, which is in a mixture with the finely divided active component.

In tablets, the active component is mixed with the carrier having the necessary binding capacity in suitable proportions and compacted in the shape and size desired.

The powders and tablets preferably contain from five or ten to about seventy percent of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as carrier providing a capsule in which the active component, with or without carriers, is surrounded by a carrier, which is thus in association with it. Similarly, cachets and lozenges are included. Tablets, powders, capsules, pills, cachets, and lozenges can be used as solid forms suitable for oral administration.

For preparing suppositories, a low melting wax, such as a mixture of fatty acid glyceride or cocoa butter, is first melted and the active component is dispersed homogeneously therein, as by stirring. The molten homogenous mixture is then poured into convenient sized moulds, allowed to cool, and thereby to solidify.

Compositions suitable for vaginal administration may be presented as pessaries, tampons, creams, gels, pastes, foams or sprays containing in addition to the active ingredient such carriers as are known in the art to be appropriate.

Liquid preparations include solutions, suspensions, and emulsions, for example, water or water-propylene glycol solutions. For example, parenteral injection liquid preparations can be formulated as solutions in aqueous polyethylene glycol solution.

The chemical compound according to the present invention may thus be formulated for parenteral administration (e.g. by injection, for example bolus injection or continuous infusion) and may be presented in unit dose form in ampoules, pre-filled syringes, small volume infusion or in multi-dose containers with an added preservative. The compositions may take such forms as suspensions, solutions, or emulsions in oily or aqueous vehicles, and may contain formulation agents such as suspending, stabilising and/or dispersing agents. Alternatively, the active ingredient may be in powder form, obtained by aseptic isolation of sterile solid or by lyophilization from solution, for constitution with a suitable vehicle, e.g. sterile, pyrogen-free water, before use.

Aqueous solutions suitable for oral use can be prepared by dissolving the active component in water and adding suitable colorants, flavours, stabilising and thickening agents, as desired.

Aqueous suspensions suitable for oral use can be made by dispersing the finely divided active component in water with viscous material, such as natural or synthetic gums, resins, methylcellulose, sodium carboxymethylcellulose, or other well known suspending agents.

Also included are solid form preparations, intended for conversion shortly before use to liquid form preparations for oral administration. Such liquid forms include solutions, suspensions, and emulsions. In addition to the active component such preparations may comprise colorants, flavours, stabilisers, buffers, artificial and natural sweeteners, dispersants, thickeners, solubilizing agents, and the like.

For topical administration to the epidermis the chemical compound of the invention may be formulated as ointments, creams or lotions, or as a transdermal patch. Ointments and creams may, for example, be formulated with an aqueous or oily base with the addition of suitable thickening and/or gelling agents. Lotions may be formulated with an aqueous or oily base and will in general also contain one or more emulsifying agents, stabilising agents, dispersing agents, suspending agents, thickening agents, or colouring agents.

Compositions suitable for topical administration in the mouth include lozenges comprising the active agent in a flavoured base, usually sucrose and acacia or tragacanth; pastilles comprising the active ingredient in an inert base such as gelatin and glycerine or sucrose and acacia; and mouthwashes comprising the active ingredient in a suitable liquid carrier.

Solutions or suspensions are applied directly to the nasal cavity by conventional means, for example with a dropper, pipette or spray. The compositions may be provided in single or multi-dose form.

Administration to the respiratory tract may also be achieved by means of an aerosol formulation in which the active ingredient is provided in a pressurised pack with a suitable propellant such as a chlorofluorocarbon (CFC) for example dichlorodifluoromethane, trichlorofluoromethane, or dichlorotetrafluoroethane, carbon dioxide, or other suitable gas. The aerosol may conveniently also contain a surfactant such as lecithin. The dose of drug may be controlled by provision of a metered valve.

Alternatively the active ingredients may be provided in the form of a dry powder, for example a powder mix of the compound in a suitable powder base such as lactose, starch, starch derivatives such as hydroxypropylmethyl cellulose and polyvinylpyrrolidone (PVP). Conveniently the powder carrier will form a gel in the nasal cavity. The powder composition may be presented in unit dose form for example in capsules or cartridges of, e.g., gelatin, or blister packs from which the powder may be administered by means of an inhaler.

In compositions intended for administration to the respiratory tract, including intranasal compositions, the compound will generally have a small particle size for example of the order of 5 microns or less. Such a particle size may be obtained by means known in the art, for example by micronization.

When desired, compositions adapted to give sustained release of the active ingredient may be employed.

The pharmaceutical preparations are preferably in unit dosage forms. In such form, the preparation is subdivided into unit doses containing appropriate quantities of the active component. The unit dosage form can be a packaged preparation, the package containing discrete quantities of preparation, such as packaged tablets, capsules, and powders in vials or ampoules. Also, the unit dosage form can be a capsule, tablet, cachet, or lozenge itself, or it can be the appropriate number of any of these in packaged form.

Tablets or capsules for oral administration and liquids for intravenous administration and continuous infusion are preferred compositions.

The pharmaceutical composition of the invention may be administered by any convenient route, which suits the desired therapy. Preferred routes of administration include oral administration, in particular in tablet, in capsule, in dragé, in powder, or in liquid form, and parenteral administration, in particular cutaneous, subcutaneous, intramuscular, or intravenous injection. The pharmaceutical composition of the invention can be manufactured by any skilled person by use of standard methods and conventional techniques appropriate to the desired formulation. When desired, compositions adapted to give sustained release of the active ingredient may be employed.

Further details on techniques for formulation and administration may be found in the latest edition of *Remington's Pharmaceutical Sciences* (Maack Publishing Co., Easton, Pa.).

The actual dosage depends on the nature and severity of the disease being treated, and is within the discretion of the physician, and may be varied by titration of the dosage to the particular circumstances of this invention to produce the desired therapeutic effect. However, it is presently contemplated that pharmaceutical compositions containing of from about 0.1 to about 500 mg of active ingredient per individual dose, preferably of from about 1 to about 100 mg, most preferred of from about 1 to about 10 mg, are suitable for therapeutic treatments.

The active ingredient may be administered in one or several doses per day. A satisfactory result can, in certain instances, be obtained at a dosage as low as 0.1 µg/kg i.v. and 1 µg/kg p.o. The upper limit of the dosage range is presently considered to be about 10 mg/kg i.v. and 100 mg/kg p.o. Preferred ranges are from about 0.1 µg/kg to about 10 mg/kg/day i.v., and from about 1 µg/kg to about 100 mg/kg/day p.o.

Methods of Therapy

In another aspect the invention provides a method for the treatment, prevention or alleviation of a disease or a disorder or a condition of a living animal body, including a human, which disease, disorder or condition is responsive to modulation of the nicotinic acetylcholine receptors, and which method comprises administering to such a living animal body, including a human, in need thereof an effective amount of a 3,9-diazabicyclo[3.3.1]nonane derivative of the invention.

The preferred medical indications contemplated according to the invention are those stated above.

It is at present contemplated that suitable dosage ranges are 0.1 to 1000 milligrams daily, 10-500 milligrams daily, and especially 30-100 milligrams daily, dependent as usual upon the exact mode of administration, form in which administered, the indication toward which the administration is directed, the subject involved and the body weight of the subject involved, and further the preference and experience of the physician or veterinarian in charge.

EXAMPLES

The invention is further illustrated with reference to the following examples, which are not intended to be in any way limiting to the scope of the invention as claimed.

All reactions involving air sensitive reagents or intermediates were performed under nitrogen and in anhydrous solvents. Magnesium sulphate was used as drying agent in the workup-procedures and solvents were evaporated under reduced pressure.

Example 1

Preparatory Example

Method A 3-(5-Chloro-pyridin-3-yl)-9-methyl-3,9-diaza-bicyclo[3.3.1]nonane fumaric acid salt (Compound A1)

A mixture of 9-methyl-3,9-diaza-bicyclo[3.3.1]nonane (1.0 g, 7.13 mmol) and 3,5-dichloropyridine (2.11 g, 14.3 mmol) was stirred at 190° C. for 72 hours. Aqueous sodium hydroxide (20 ml, 1 M) was added followed by extraction with dichloromethane (3×10 ml). The crude product was purified by silica gel column chromatography using a solvent mixture of dichloromethane, methanol and aqueous ammonia (9:1:1%). Yield 340 mg (19%). The corresponding salt was obtained by addition of a diethyl ether and methanol mixture (9:1) saturated with fumaric acid. Mp 170.9-173.1° C. LC-ESI-HRMS of [M+H]+ shows 252.1281 Da. Calc. 252.12675 Da, dev. 5.4 ppm.

9-Methyl-3-pyridin-3-yl-3,9-diaza-bicyclo[3.3.1]nonane fumaric acid salt (Compound A2)

Was prepared according to Method A using a sealed steel-vessel and the reaction temperature 210° C. Mp 127.0-144.9° C. LC-ESI-HRMS of [M+H]+ shows 218.1661 Da. Calc. 218.165722 Da, dev. 1.7 ppm.

3-(5-Chloro-pyridin-2-yl)-9-methyl-3,9-diaza-bicyclo[3.3.1]nonane fumaric acid salt (Compound A3)

Prepared according to Method A. LC-ESI-HRMS of [M+H]+ shows 252.1267 Da. Calc. 252.12675 Da, dev. −0.2 ppm.

3-(6-Chloro-pyridin-2-yl)-9-methyl-3,9-diaza-bicyclo[3.3.1]nonane fumaric acid salt (Compound A4)

Prepared according to Method A. LC-ESI-HRMS of [M+H]+ shows 252.1255 Da. Calc. 252.12675 Da, dev. −5 ppm.

3-(6-Bromo-p-2-yl)-9-methyl-3,9-diaza-bicyclo[3.3.1]nonane fumaric acid salt (Compound A5)

Prepared according to Method A. LC-ESI-HRMS of [M+H]+ shows 296.0749 Da. Calc. 296.076235 Da, dev. −4.5 ppm.

3-(5-Bromo-pyridin-2-yl)-9-methyl-3,9-diaza-bicyclo[3.3.1]nonane fumaric acid salt (Compound A6)

Prepared according to Method A. LC-ESI-HRMS of [M+H]+ shows 296.0778 Da. Calc. 296.076235 Da, dev. 5.3 ppm.

3-(6-Chloro-pyridazin-3-yl)-9-methyl-3,9-diaza-bicyclo[3.3.1]nonane fumaric acid salt (Compound A7)

Prepared according to Method A using dioxane as solvent and reflux conditions. LC-ESI-HRMS of [M+H]+ shows 253.1213 Da. Calc. 253.121999 Da, dev. −2.8 ppm.

3-(6-Bromo-pyridazin-3-yl)-9-methyl-3,9-diaza-bicyclo[3.3.1]nonane free base (Compound A8)

Prepared according to Method A using dioxane as solvent and reflux conditions. LC-ESI-HRMS of [M+H]+ shows 297.0713 Da. Calc. 297.071484 Da, dev. −0.6 ppm.

3-(5-Ethoxy-pyridin-3-yl)-9-methyl-3,9-diaza-bicyclo[3.3.1]nonane fumaric acid salt (Compound A9)

Prepared according to Method A using potassium tert-butoxide as base and 1,2-dimethoxyethane as solvent at reflux. LC-ESI-HRMS of [M+H]+ shows 262.1926 Da. Calc. 262.191937 Da, dev. 2.5 ppm.

3-(5-Methoxy-pyridin-3-yl)-9-methyl-3,9-diaza-bicyclo[3.3.1]nonane fumaric acid salt (Compound A10)

Prepared according to Method A using potassium tert-butoxide as base and 1,2-dimethoxyethane as solvent at reflux. LC-ESI-HRMS of [M+H]+ shows 248.1763 Da. Calc. 248.176287 Da, dev. 0.1 ppm.

9-Methyl-3-(5-vinyloxy-pyridin-3-yl)-3,9-diaza-bicyclo[3.3.1]nonane fumaric acid salt (Compound A11)

Prepared according to Method A using potassium tert-butoxide as base and 1,2-dimethoxyethane as solvent at reflux. LC-ESI-HRMS of [M+H]+ shows 260.1767 Da. Calc. 260.176287 Da, dev. 1.6 ppm.

9-Methyl-3-{5-[((Z)-propenyl)oxy]-pyridin-3-yl}-3,9-diaza-bicyclo[3.3.1]nonane fumaric acid salt (Compound A12)

Prepared according to Method A using potassium tert-butoxide as base and 1,2-dimethoxyethane as solvent at reflux. LC-ESI-HRMS of [M+H]+ shows 274.192 Da. Calc. 274.191937 Da, dev. 0.2 ppm.

3-(5-Iodo-pyridin-2-yl)-9-methyl-3,9-diaza-bicyclo[3.3.1]nonane free base (Compound A13)

Prepared according to Method A. LC-ESI-HRMS of [M+H]+ shows 344.0631 Da. Calc. 344.062397 Da, dev. 2 ppm.

3-(3,5-Dichloro-pyridin-2-yl)-9-methyl-3,9-diaza-bicyclo[3.3.1]nonane free base (Compound A14)

Prepared according to Method A. LC-ESI-HRMS of [M+H]+ shows 286.0875 Da. Calc. 286.087778 Da, dev. −1 ppm.

1-[6-(9-Methyl-3,9-diaza-bicyclo[3.3.1]non-3-yl)-pyridin-2-yl]-ethanone free base (Compound A15)

Prepared according to Method A from 5-acetyl-2-bromopyridine and tributylamine. LC-ESI-HRMS of [M+H]+ shows 260.1751 Da. Calc. 260.176287 Da, dev. −4.6 ppm.

1-[6-(9-Methyl-3,9-diaza-bicyclo[3.3.1]non-3-yl)-pyridin-2-yl]-ethanone hydrochloric acid salt (Compound A16)

Prepared according to Method A from 2-acetyl-6-bromopyridine and tributylamine. LC-ESI-HRMS of [M+H]+ shows 260.1774 Da. Calc. 260.176287 Da, dev. 4.3 ppm.

3-(5-Bromo-pyrimidin-2-yl)-9-methyl-3,9-diaza-bicyclo[3.3.1]nonane free base (Compound A17)

Prepared according to Method A using dioxane as solvent and reflux conditions. LC-ESI-HRMS of [M+H]+ shows 297.0702 Da. Calc. 297.071484 Da, dev. −4.3 ppm.

3-(6-Chloro-pyridin-3-yl)-9-methyl-3,9-diaza-bicyclo[3.3.1]nonane fumaric acid salt (Compound A18)

Prepared according to Method A, from 2-chloro-5-iodopyridine using PdCl2(PPh3)2 as catalyst, potassium tert-butoxide and DME as solvent at reflux conditions. LC-ESI-HRMS of [M+H]+ shows 252.128 Da. Calc. 252.12675 Da, dev. 5 ppm.

Method B

3-Pyridin-3-yl-3,9-diaza-bicyclo[3.3.1]nonane fumaric acid salt (Compound B1)

A mixture of 9-methyl-3-pyridin-3-yl-3,9-diaza-bicyclo[3.3.1]nonane (1.0 g, 4.46 mmol), 2,2,2-trichloroethylchloroformate (2.8 g, 13.4 mmol) and toluene (30 ml) was stirred at reflux for 15 hours. Water (30 ml) was added and the phases were separated. The organic phase was evaporated. Acetic acid (15 ml) and water (15 ml) and zinc powder (1.46 g, 22.3 mmol) was added. The mixture was stirred for 15 hours. Aqueous sodium hydroxide (20 ml, 1M) was added followed by extraction with dichloromethane (3×10 ml). The crude product was purified by silica gel column chromatography using a solvent mixture of dichloromethane, methanol and aqueous ammonia (9:1:1%). The corresponding salt was obtained by addition of a diethyl ether and methanol mixture (9:1) saturated with fumaric acid. Yield 57 mg (3%). Mp 160.1-163.1° C. LC-ESI-HRMS of [M+H]+ shows 204.1501 Da. Calc. 204.150072 Da, dev. 0.1 ppm.

3-(5-Chloro-pyridin-2-yl)-3,9-diaza-bicyclo[3.3.1] nonane hydrochloric acid salt (Compound B2)

Prepared according to Method B. LC-ESI-HRMS of [M+H]+ shows 238.1113 Da. Calc. 238.1111 Da, dev. 0.8 ppm.

3-Pyridin-2-yl-3,9-diaza-bicyclo[3.3.1]nonane free base (Compound B3)

Prepared according to Method B. LC-ESI-HRMS of [M+H]+ shows 204.1498 Da. Calc. 204.150072 Da, dev. -1.3 ppm.

3-(3,5-Dichloro-pyridin-2-yl)-3,9-diaza-bicyclo [3.3.1]nonane free base (Compound B4)

Prepared according to Method B. LC-ESI-HRMS of [M+H]+ shows 272.0724 Da. Calc. 272.072128 Da, dev. 1 ppm.

Method C

9-Methyl-3-pyridazin-3-yl-3,9-diaza-bicyclo[3.3.1] nonane fumaric acid salt (Compound C1)

A mixture of 3-(6-chloro-pyridazin-3-yl)-9-methyl-3,9-diaza-bicyclo[3.3.1]nonane (1.16 g, 4.6 mmol), palladium on carbon (5%, 400 mg) and ethanol (50 ml, 96%) was stirred under hydrogen and filtered through celite, followed by evaporation. The crude product was purified by silica gel column chromatography using a solvent mixture of dichloromethane, methanol and aqueous ammonia (9:1:1). The corresponding salt was obtained by addition of a diethyl ether and methanol mixture (9:1) saturated with fumaric acid. Yield 261 mg (95%). LC-ESI-HRMS of [M+H]+ shows 219.1601 Da. Calc. 219.160971 Da, dev. -4 ppm.

Method D

3-(6-Bromo-pyridin-3-yl)-9-methyl-3,9-diaza-bicyclo[3.3.1]nonane free base (Compound D1)

A mixture of 9-methyl-3-pyridin-3-yl-3,9-diaza-bicyclo [3.3.1]nonane (1.38, 6.2 mmol) and acetonitrile (40 ml) was cooled to 0° C. N-bromo-succinimide (1.1 g, 6.2 mmol) in acetonitrile (20 ml) was added during 2 h. The mixture was stirred over night at room-temperature. The mixture was evaporated. Aqueous sodium hydroxide (20 ml, 1 M) was added followed by extraction with dichloromethane (3×10 ml). The product was purified by silica gel column chromatography using a solvent mixture of dichloromethane, methanol and aqueous ammonia (9:1:1%). Yield 900 mg (49%). LC-ESI-HRMS of [M+H]+ shows 296.0757 Da. Calc. 296.076235 Da, dev. -1.8 ppm.

3-(6-Fluoro-pyridin-3-yl)-9-methyl-3,9-diaza-bicyclo[3.3.1]nonane (Compound D2)

Is prepared according to Method D.

Method E

9,9-Dimethyl-3-(6-bromo-pyridin-3-yl)-3,9-diazabicyclo[3.3.1]nonane onium iodide (Compound E1)

A mixture of 3-(6-bromo-pyridin-3-yl)-9-methyl-3,9-diaza-bicyclo[3.3.1] (0.20 g, 0.67 mmol) in dichloromethane (10 ml) was cooled to -70° C. Iodomethane (95.8 mg, 0.67 mmol) was added at -70° C. and stirred for 1 h at -70° C. The mixture was allowed to reach room-temperature and was stirred overnight. The mixture was evaporated and a mixture of diethylether and methanol (5%) was added and the product was stirred and isolated by filtration. Yield 220 mg (74%). LC-ESI-HRMS of M+ shows 310.0922 Da. Calc. 310.0919 Da, dev. 1 ppm.

Example 2

Biological Activity

In Vitro Inhibition of $^3$H-Cytisine Binding

Molecular biology studies have elucidated that there are at least ten nicotinic receptor genes in the brain. The predominant subtype with high affinity for nicotine is comprised of $\alpha_4$ and $\beta_2$ subunits. nAChRs of the latter type can selectively be labelled by the nicotine agonist $^3$H-cytisine.

A standard assay for determining in vitro inhibition of $^3$H-cytisine binding is described in e.g. WO 02/096911. When subjected to this test the compounds of the invention show inhibitory activity on the micromolar or sub-micromolar range.

The results of such determinations are presented in Table 1 below.

TABLE 1

In vitro Inhibition of $^3$H-cytisine Binding

| Compound No. | $IC_{50}$ (μM) |
| --- | --- |
| A1 | 0.0063 |
| B1 | 0.0025 |
| C1 | 0.46 |

The invention claimed is:
1. A 3,9-diaza-bicyclo[3.3.1]nonane compound of formula (I):

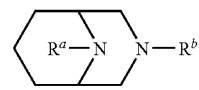

any of its stereoisomers or any mixture of its stereoisomers, or a pharmaceutically acceptable salt thereof; wherein
$R^a$ represents hydrogen or alkyl; which alkyl is optionally substituted with one or more substituents independently selected from the group consisting of halo, trifluoromethyl, trifluoromethoxy, cyano, hydroxy, amino, nitro, alkoxy, cycloalkoxy, alkyl, cycloalkyl, cycloalkyl-alkyl, alkenyl and alkynyl; and R$^b$ represents a pyridyl, pyrimidyl, pyrazinyl, or pyridazinyl group; which pyridyl, pyrimidyl, pyrazinyl, or pyridazinyl group is optionally substituted with one or more substituents independently selected from the group consisting of halo, trifluoromethyl, trifluoromethoxy, cyano, nitro, hydroxy, alkoxy, cycloalkoxy, alkoxy-alkyl, cycloalkoxy-alkyl, alkenoxy, methylenedioxy, ethylenedioxy, alkyl, cycloalkyl, cycloalkyl-alkyl, alkenyl, alkynyl, alkyl-carbonyl, —NR'R", —(C=O)NR'R" and —NR'(C=O)R"; wherein R' and R" independent of each other are hydrogen or alkyl.

2. The 3,9-diaza-bicyclo[3.3.1]nonane compound of claim 1, or a pharmaceutically acceptable salt thereof, wherein R$^a$ represents hydrogen or alkyl.

3. The 3,9-diaza-bicyclo[3.3.1]nonane compound of claim 1, or a pharmaceutically acceptable salt thereof, wherein the pyridyl, pyrimidyl, pryazinyl, or pyridazinvi group is optionally substituted once or twice with substituents selected from halo, trifluoromethyl, trifluoromethoxy, cyano, nitro, hydroxy, alkoxy, alkenoxy, alkyl, cycloalkyl and alkyl-carbonyl.

4. The 3,9-diaza-bicyclo[3.3.1]nonane compound of claim 1, or a pharmaceutically acceptable salt thereof, wherein R$^b$ represents pyridinyl, pyridazinyl or pyrimidinyl, optionally substituted once or twice with halo, trifluoromethyl, alkoxy, alkenoxy and/or alkyl-carbonyl.

5. The 3,9-diaza-bicyclo[3.3.1]nonane compound of claim 1, which is
3-(5-Chloro-pyridin-3-yl)-9-methyl-3,9-diaza-bicyclo[3.3.1]nonane;
9-Methyl-3-pyridin-3-yl-3,9-diaza-bicyclo[3.3.1]nonane;
3-Pyridin-3-yl-3,9-diaza-bicyclo[3.3.1]nonane;
3-(5-Chloro-pyridin-2-yl)-9-methyl-3,9-diaza-bicyclo[3.3.1]nonane;
3-(6-Chloro-pyridin-2-yl)-9-methyl-3,9-diaza-bicyclo[3.3.1]nonane;
3-(6-Bromo-pyridin-2-yl)-9-methyl-3,9-diaza-bicyclo[3.3.1]nonane;
3-(5-Bromo-pyridin-2-yl)-9-methyl-3,9-diaza-bicyclo[3.3.1]nonane;
3-(6-Chloro-pyridazin-3-yl)-9-methyl-3,9-diaza-bicyclo[3.3.1]nonane;
3-(6-Bromo-pyridazin-3-yl)-9-methyl-3,9-diaza-bicyclo[3.3.1]nonane;
3-(5-Ethoxy-pyridin-3-yl)-9-methyl-3,9-diaza-bicyclo[3.3.1]nonane;
3-(5-Methoxy-pyridin-3-yl)-9-methyl-3,9-diaza-bicyclo[3.3.1]nonane;
9-Methyl-3-(5-vinyloxy-pyridin-3-yl)-3,9-diaza-bicyclo[3.3.1]nonane;
9-Methyl-3-{5-[((Z)-propenyl)oxy]-pyridin-3-yl}-3,9-diaza-bicyclo[3.3.1]nonane;
3-(5-Iodo-pyridin-2-yl)-9-methyl-3,9-diaza-bicyclo[3.3.1]nonane;
3-(3,5-Dichloro-pyridin-2-yl)-9-methyl-3,9-diaza-bicyclo[3.3.1]nonane;
1-[6-(9-Methyl-3,9-diaza-bicyclo[3.3.1]non-3-yl)-pyridin-2-yl]-ethanone;
1-[6-(9-Methyl-3,9-diaza-bicyclo[3.3.1]non-3-yl)-pyridin-2-yl]-ethanone;
3-(5-Bromo-pyrimidin-2-yl)-9-methyl-3,9-diaza-bicyclo[3.3.1]nonane;
3-(6-Chloro-pyridin-3-yl)-9-methyl-3,9-diaza-bicyclo[3.3.1]nonane;
3-(5-Chloro-pyridin-2-yl)-3,9-diaza-bicyclo[3.3.1]nonane;
3-Pyridin-2-yl-3,9-diaza-bicyclo[3.3.1]nonane;
3-(3,5-Dichloro-pyridin-2-yl)-3,9-diaza-bicyclo[3.3.1]nonane;
9-Methyl-3-pyridazin-3-yl-3,9-diaza-bicyclo[3.3.1]nonane;
3-(6-Bromo-pyridin-3-yl)-9-methyl-3,9-diaza-bicyclo[3.3.1]nonane; or
9,9-Dimethyl-3-(6-bromo-pyridin-3-yl)-3,9-diaza-bicyclo[3.3.1]nonane;
or a pharmaceutically acceptable salt thereof.

6. The compound of claim 5 which is 3-pyridin-3-yl-3,9-diaza-bicyclo[3.3.1]nonane
or a pharmaceutically acceptable salt thereof.

7. A pharmaceutical composition, comprising a therapeutically effective amount of a 3,9-diaza-bicyclo[3.3.1]nonane compound of claim 1, any of its stereoisomers or any mixture of its stereoisomers, or a pharmaceutically acceptable salt thereof, together with at least one pharmaceutically acceptable carrier, excipient or diluent.

* * * * *